US008512361B2

(12) United States Patent
Grönberg et al.

(10) Patent No.: US 8,512,361 B2
(45) Date of Patent: Aug. 20, 2013

(54) DEVICE AND A METHOD FOR ANASTOMOSIS

(75) Inventors: Anders Grönberg, Halmstad (SE); Henrik Thorlacius, Lund (SE)

(73) Assignee: Carponovum AB, Lund (SE)

( * ) Notice: Subject to any disclaimer, the term of this patent is extended or adjusted under 35 U.S.C. 154(b) by 1044 days.

(21) Appl. No.: 12/297,694

(22) PCT Filed: Apr. 23, 2007

(86) PCT No.: PCT/EP2007/053965
§ 371 (c)(1),
(2), (4) Date: Oct. 20, 2008

(87) PCT Pub. No.: WO2007/122223
PCT Pub. Date: Nov. 1, 2007

(65) Prior Publication Data
US 2009/0138030 A1 May 28, 2009

(30) Foreign Application Priority Data
Apr. 21, 2006 (SE) ....................... 0600868

(51) Int. Cl.
*A61B 17/08* (2006.01)
(52) U.S. Cl.
USPC ............................ 606/153; 606/142; 606/151
(58) Field of Classification Search
USPC .................................... 606/142, 139, 151, 153
See application file for complete search history.

(56) References Cited

U.S. PATENT DOCUMENTS

| 2,434,030 A | 1/1948 | Yeomans |
| 2,453,056 A | 11/1948 | Zack |
| 3,974,835 A | 8/1976 | Hardy, Jr. |
| 4,055,186 A * | 10/1977 | Leveen .......................... 606/153 |

(Continued)

FOREIGN PATENT DOCUMENTS

| CA | 1243246 A1 | 10/1988 |
| EP | 0 119 848 | 9/1984 |

(Continued)

OTHER PUBLICATIONS

International Search Report for International Application No. PCT/EP2007/053961 mailed Jan. 25, 2008.

(Continued)

*Primary Examiner* — Corrine M McDermott
*Assistant Examiner* — Alexander Orkin
(74) *Attorney, Agent, or Firm* — Polster, Lieder, Woodruff & Lucchesi, LC

(57) ABSTRACT

Devices and methods for anastomosis are provided. The devices can include a first and a second member of a generally hollow open configuration. The first and second members may each include a rigid part and an elastic part arranged circumferentially of the rigid part. The devices may also include a connection member for interlocking the first and second members such that anastomosis is obtained at a contact area in-between the elastic parts. The methods can include arranging an elastic part inside a tubular structure at a first end of the tubular structure, folding an edge of the first end over the elastic part, and mounting the elastic part on a rigid part, forming a first member. This may be repeated at a second end of the tubular structure, forming a second member, and the first and second members may be locked to each other by a connection member.

3 Claims, 11 Drawing Sheets

(56) References Cited

U.S. PATENT DOCUMENTS

| | | | |
|---|---|---|---|
| 4,154,241 A * | 5/1979 | Rudie | 606/153 |
| 4,657,019 A * | 4/1987 | Walsh et al. | 606/153 |
| 5,697,943 A | 12/1997 | Sauer et al. | |
| 5,857,585 A | 1/1999 | Tolkoff et al. | |
| 6,068,636 A | 5/2000 | Chen | |
| 6,517,556 B1 * | 2/2003 | Monassevitch | 606/151 |
| 6,666,873 B1 * | 12/2003 | Cassell | 606/153 |
| 6,682,540 B1 * | 1/2004 | Sancoff et al. | 606/153 |
| 7,285,125 B2 * | 10/2007 | Viola | 606/153 |
| 2002/0099394 A1 * | 7/2002 | Houser et al. | 606/153 |
| 2004/0015179 A1 | 1/2004 | Monassevitch et al. | |
| 2006/0004394 A1 * | 1/2006 | Amarant | 606/153 |
| 2007/0142850 A1 * | 6/2007 | Fowler | 606/153 |

FOREIGN PATENT DOCUMENTS

| | | |
|---|---|---|
| JP | 59177039 A | 10/1984 |
| WO | WO 2004/008937 A2 | 1/2004 |
| WO | WO 2007/122220 A3 | 11/2007 |

OTHER PUBLICATIONS

International Search Report for International Application No. PCT/EP2007/053965 mailed Sep. 3, 2007.

U.S. Appl. No. 12/297,692, filed Oct. 20, 2008 by Gronberg, Anders et al.

Office Action dated Apr. 11, 2011, received in U.S. Appl. No. 12/297,692, filed Oct. 20, 2008.

* cited by examiner

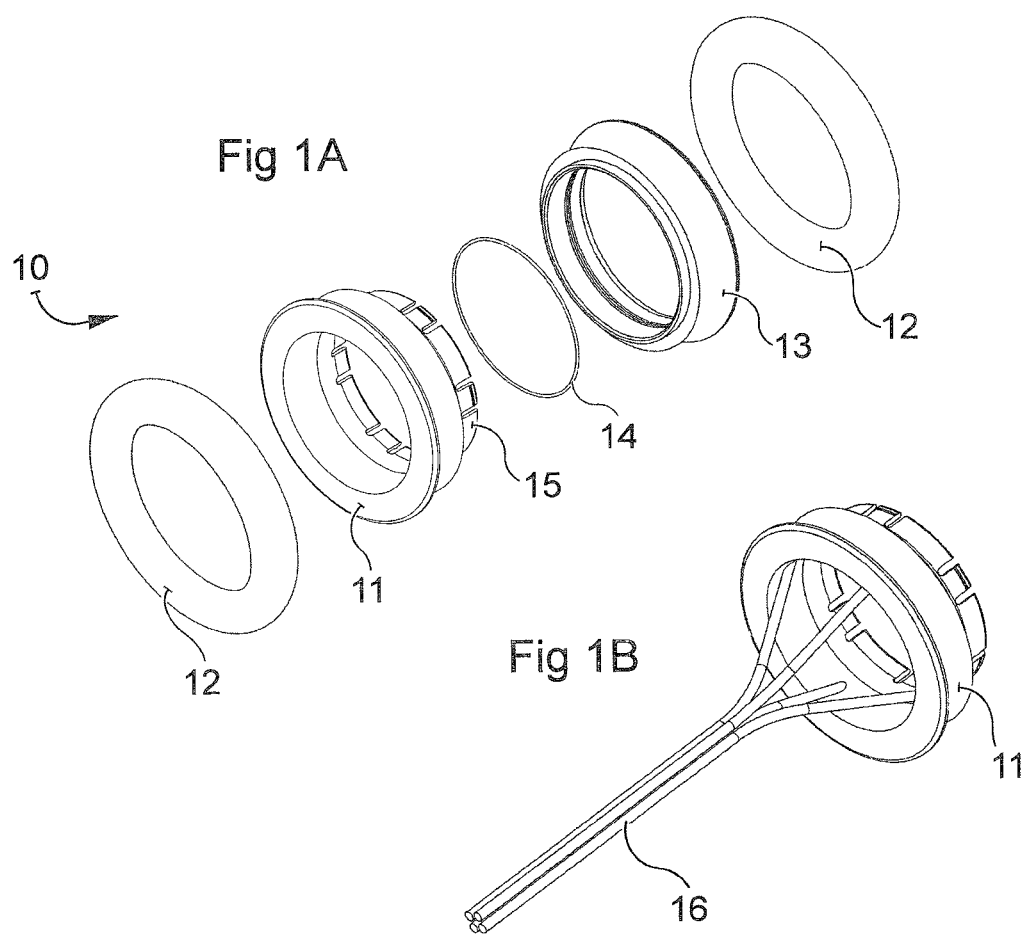

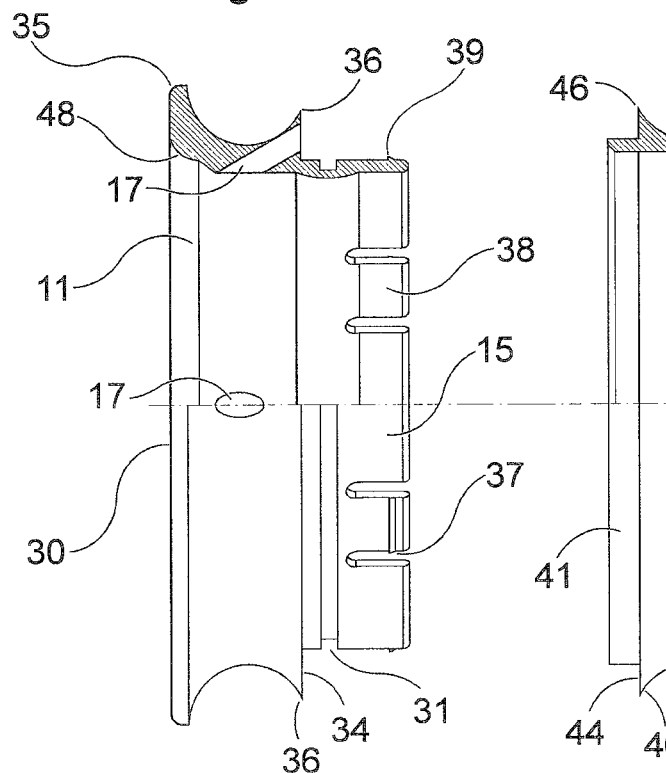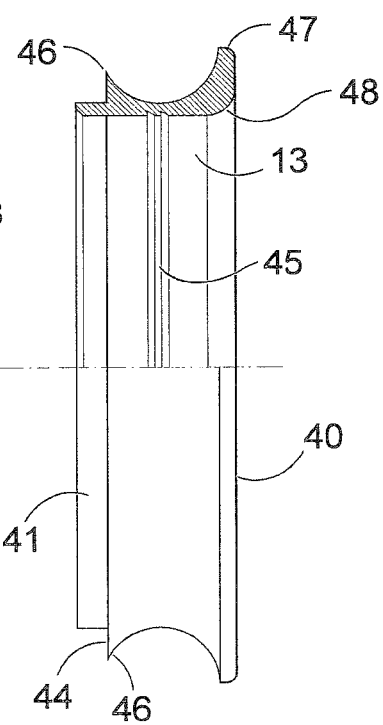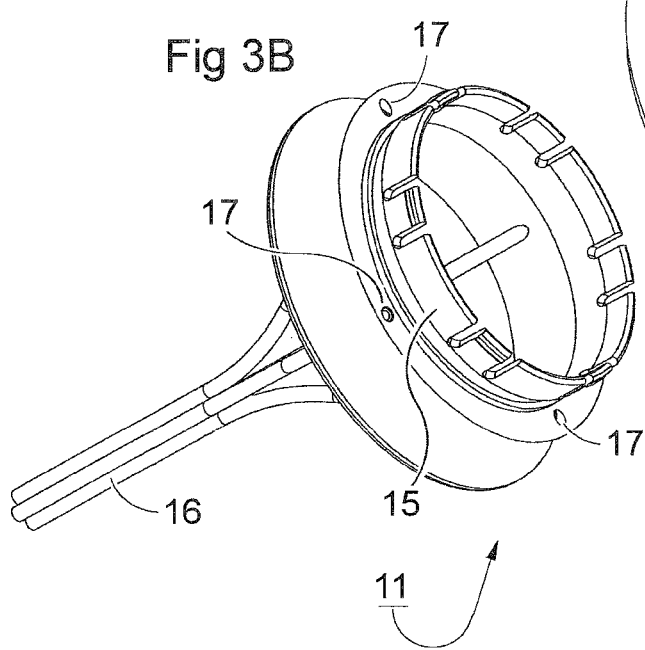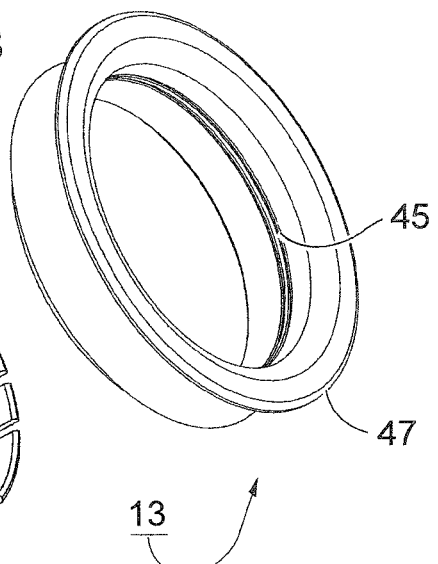

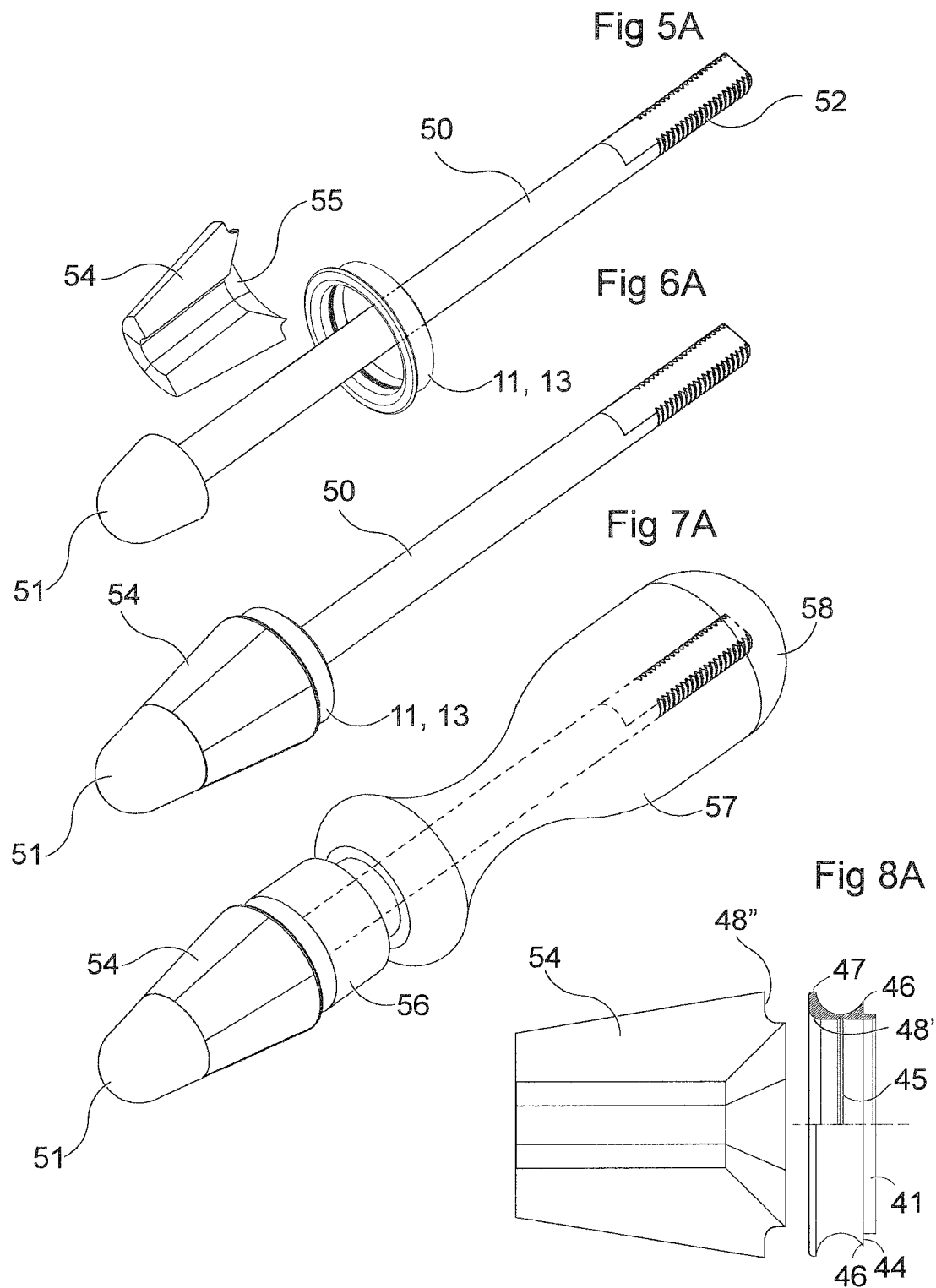

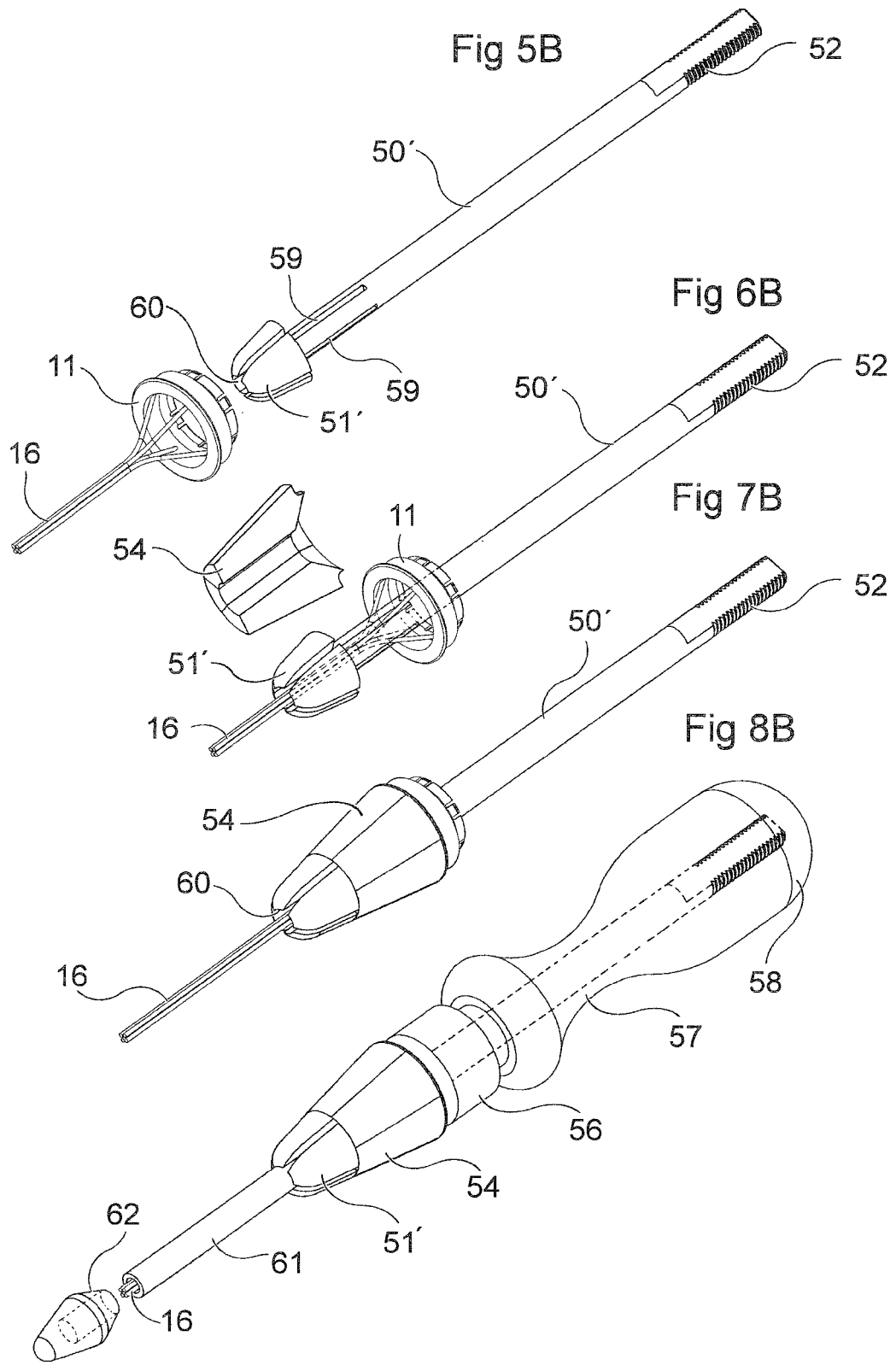

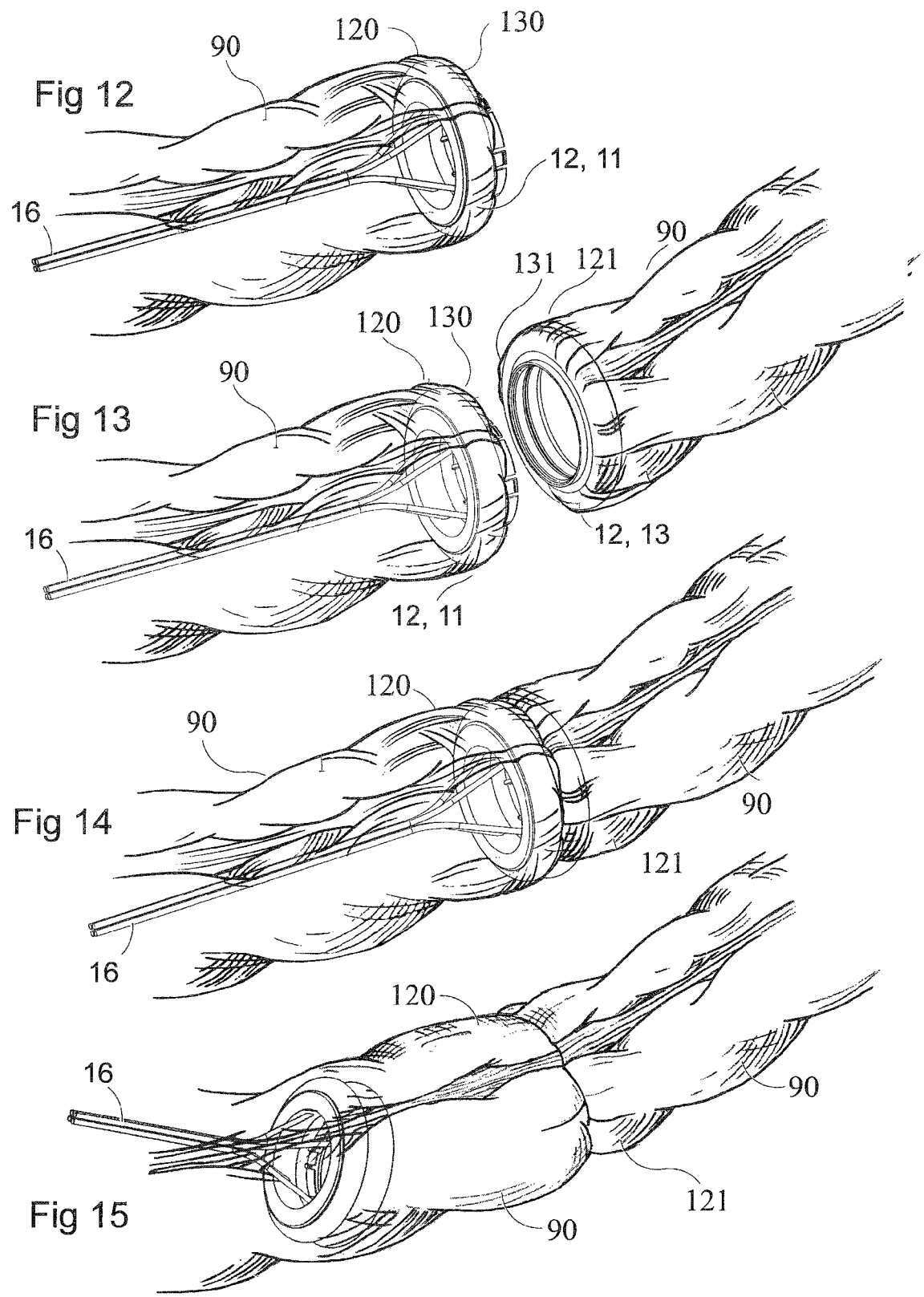

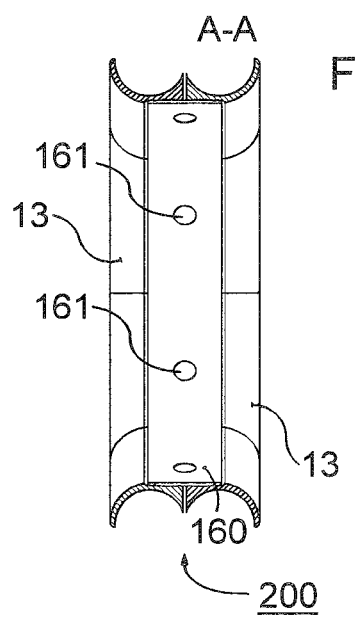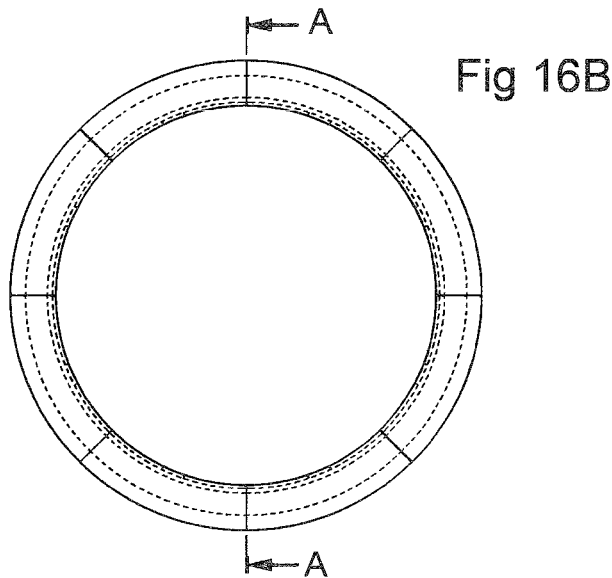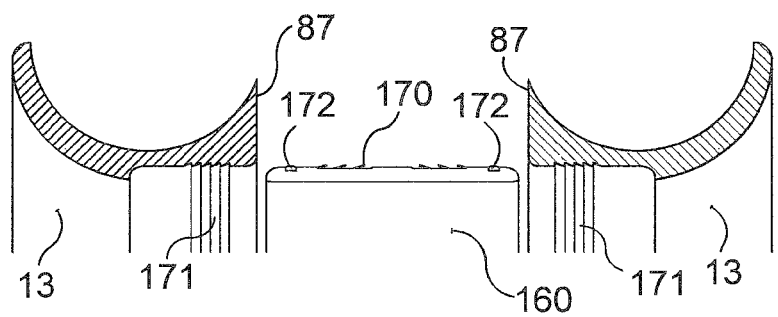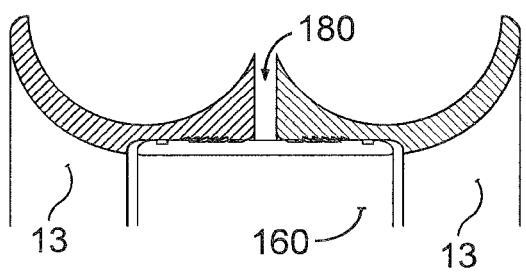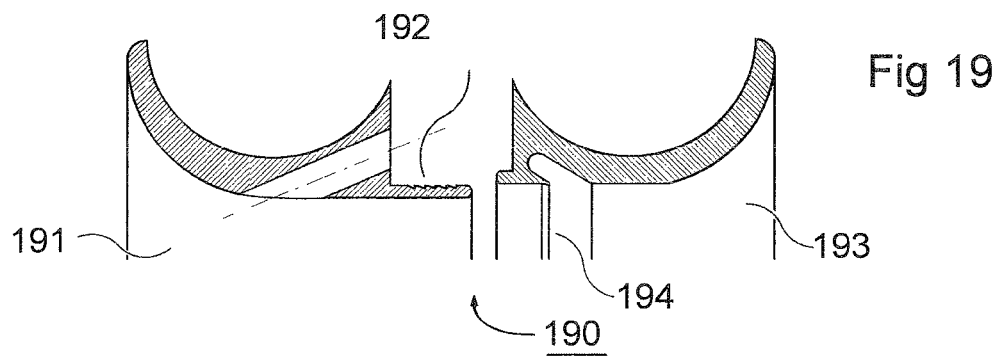

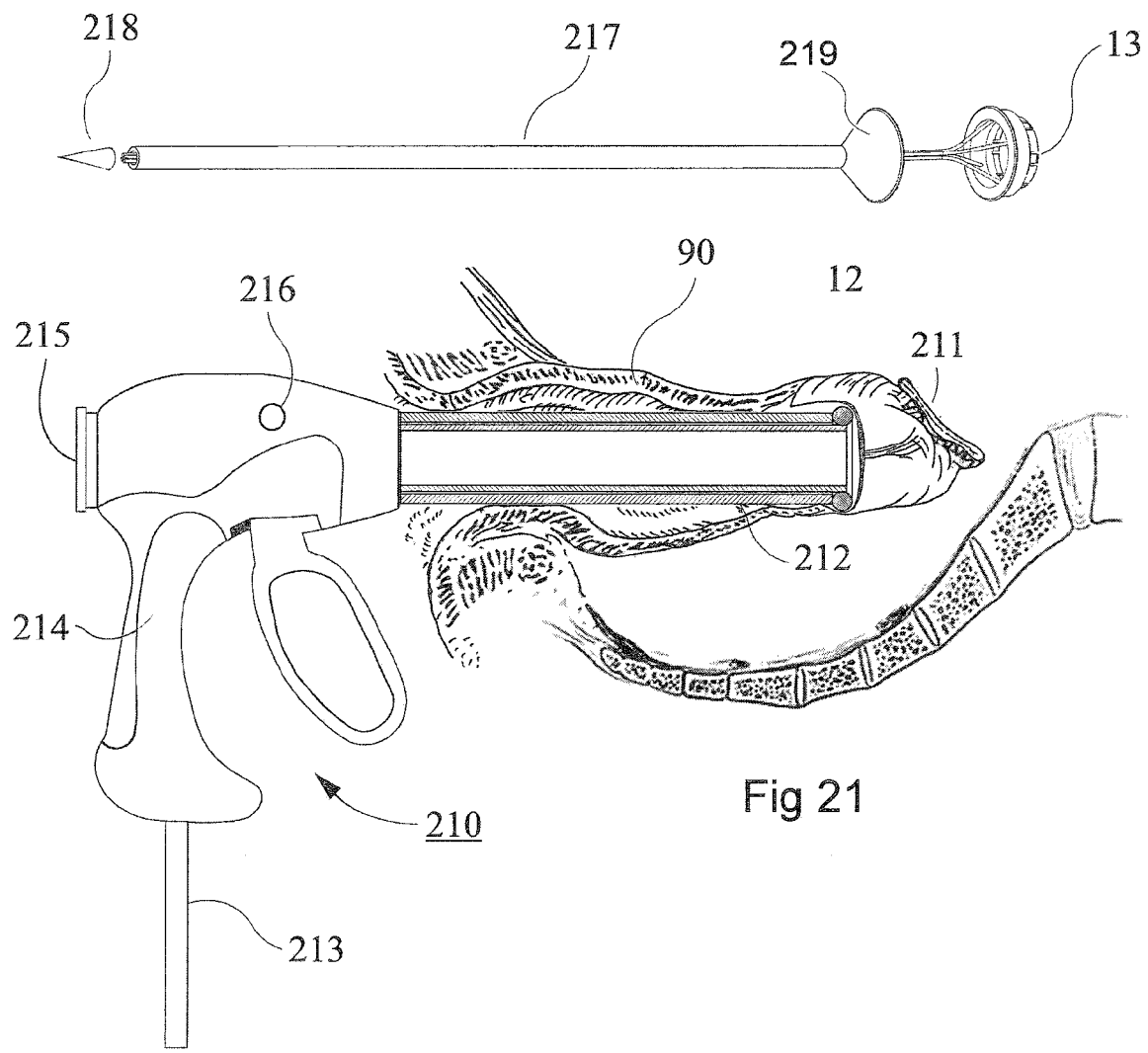

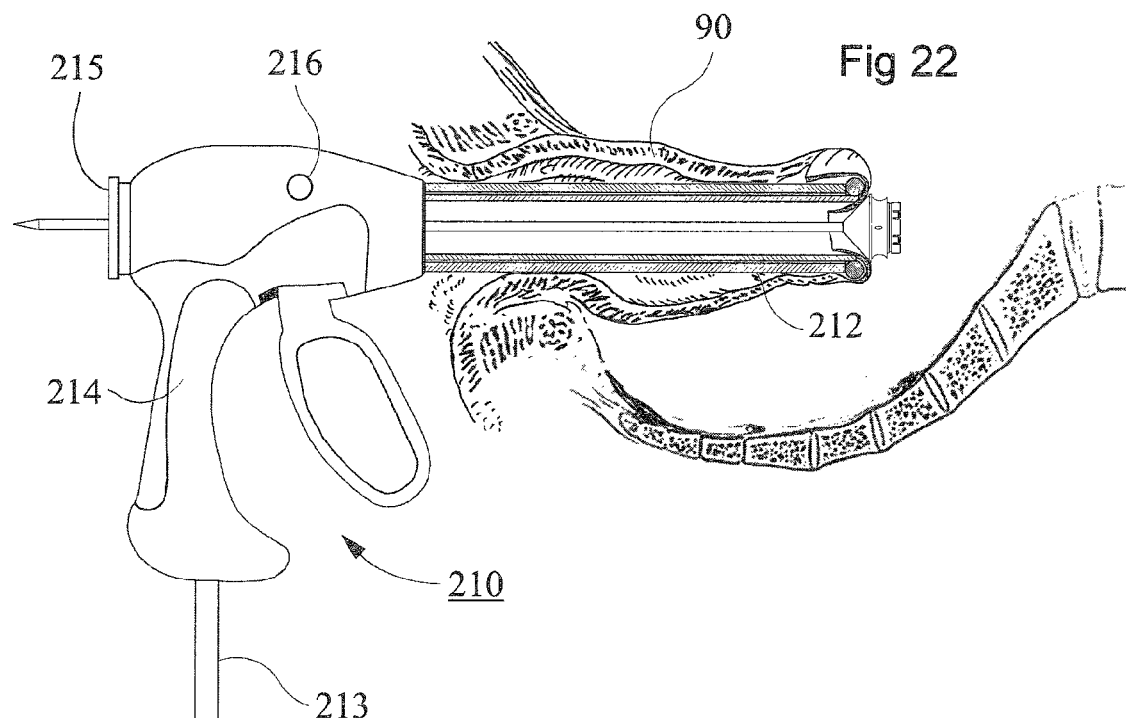
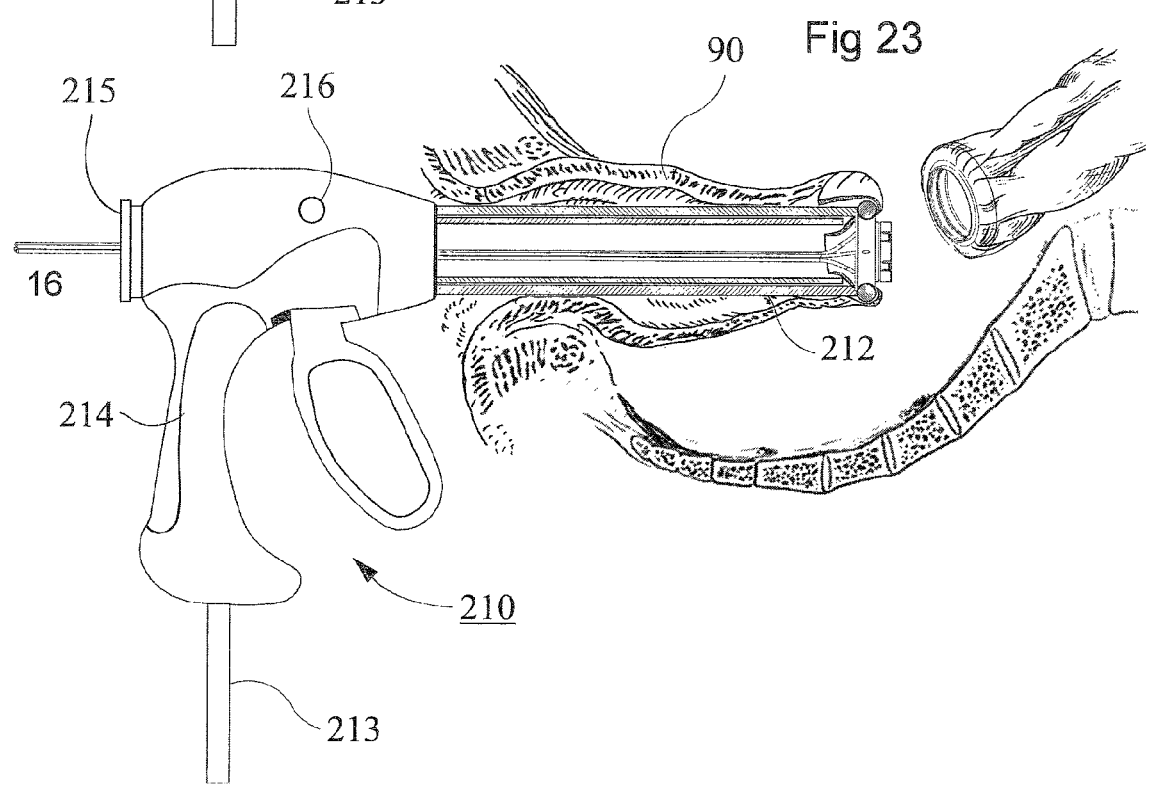

DEVICE AND A METHOD FOR ANASTOMOSIS

TECHNICAL FIELD

The present invention relates to anastomosis of a living tissue, and more particularly to a device for compression anastomosis of tubular structures. Furthermore, the invention relates to a method for mounting the device to a tubular structure.

BACKGROUND OF THE INVENTION

Colorectal cancer is the third most frequent type of cancer in the world having an occurrence of about 1 million new cases every year. The incidents of cancer are considerably more frequent in the industrial part of the world.

Current techniques for mechanically performing anastomosis of hollow organs use circular mechanical staplers, which execute the connection of the tissue edges of the dissected hollow organ by metallic or plastic staples. A wide variety of surgical staplers have been developed for gastric, oesophageal and intestinal surgery. In performing surgical anastomotic stapling, generally two pieces of the hollow organ are joined by a ring of staples with a closed loopstapler. End to end anastomoses are generally performed by intraluminal surgical staplers that deliver a pair of staggered rings of staples. During this process, a circular knife blade is used to separate the tissue that is held within the circular ring. The separated tissue is then removed with the stapler to form a circular opening within the lumen along the stapling line.

A major issue regarding anastomosis healing is the blood circulation of the anastomosis during the healing process. Despite substantial development of surgical techniques during the last decades, morbidity and mortality after resections in the gastrointestinal tract, e.g. due to anastomotic leakage, remain as serious problems. Ischemia and inflammation, which are natural parts of the healing process, may cause leakage and secondary infection that may be fatal for the patient in the stapling area. Therefore, it has become common practice to relieve the pressure from the anastomosis by performing a deviating stoma, especially when the anastomosis is carried out in the lower part of colon and in rectum. By relieving pressure and faecal stream from the anastomosis during the healing process, the leakage incident may be reduced and fatal consequences of anastomotic dehiscence can be avoided. The inconvenience for the patient is obvious, since the patient must have a temporary stoma for a time period of about 3-6 months, and then has to undergo a second surgery in order to close the stoma. Unfortunately in many cases, the closure of the stoma cannot be reversed and the patient is forced to live with a permanent stoma leading to lower quality of life associated with increased costs.

Another problem arising from stapling of anastomosis is anastomotic stenosis. The critical area for healing is the contact area between the two ends of the hollow structure to be connected. The connection has to be liquid proof, and the cross section of the lumen should be as wide and flexible as the original lumen. The size of the stapler determines the size of the lumen and thus the contact area between the ends. Surgical staplers create a smaller and more rigid opening compared to the cross section of the original lumen due to the staples inside the hollow structure connecting the two ends thereof, i.e. a collar may be formed that may lead to stenosis. For solving this problem repeated need for dilatation is required.

Another disadvantage associated with mechanical staplers, is that there is no fast, simple and reliable method to control anastomotic insufficiency, which at late discovery can result in abdominal sepsis.

Furthermore, staplers require an incision in the intestine in order to insert the instrument into the bowel lumen. This additional incision increases the duration of the operation and the risks associated with surgery, e.g. secondary infections and anastomotic leakage.

The stapler itself is a critical link, since there are several severe problems connected with the use of mechanical staplers in surgical anastomotic stapling, such as anastomotic leakage and anastomotic stenosis. Other disadvantages are high consumption of time and expensive instruments for the performance.

U.S. Pat. No. 5,931,057 discloses a compression anastomosis assembly of interlocking members for use in achieving anastomosis of tubular organs. The assembly has a locking feature to prevent inadvertent disassembly of installed coupled members. One assembly member includes a cutting guide and a cutting ring. There may be difficulties to uniformly arrange the tubular organ into the assembly at installation, since two sheets of the tubular organ are overlapping each other at arrangement between two members of the assembly, which poses a risk for leakage.

DISCLOSURE OF THE INVENTION

An object of the present invention is to eliminate at least one of the drawbacks mentioned above, which is achieved by assigning to the device the characteristics according to claim 1.

A further object of the invention is to provide a method for mounting the device to a tubular structure.

According to one aspect of the invention, there is provided a device for anastomosis of a tubular structure comprising members of a generally hollow open configuration. The device comprises a first member and a second member, wherein the first and second member each comprises a rigid part and an elastic part, respectively, and a connection member for locking the first and second member to each other. According to a first embodiment, the connection member is integral with the rigid part of the first member, and is provided with longitudinal slits forming tongues there between, wherein at least one tongue is provided with an outward protrusion. According to a second embodiment, the connection member is separated from the first and second members.

The rigid parts have an outer surface that is partly semi-circular in cross section, wherein the diameter at a non-connecting end is larger than or equal to the diameter at a connecting end, and the latter diameter ends in an edge. A distance is formed between the elastic parts, when the first and second members are connected to each other. A cavity is formed between the rigid parts and the connection member and the tubular structure when arranged in the device.

The elastic parts are essentially circular rings, and are made of a polymeric material, for example a biocompatible and/or a biodegradable material. According to another aspect of the invention, there is provided a method for mounting the device to a tubular structure having a first end and a second end to be connected, comprising the steps of arranging a first elastic part inside the tubular structure at the first end and folding the edge of the first end over the first elastic part, then mounting the first elastic part on a first rigid part forming a first member with the tubular structure arranged between the first elastic part and the first rigid part, and arranging a second elastic part inside the tubular structure at the second end and folding the edge of the second end over the second elastic part, then mounting the second elastic part on a second rigid part forming a second member with the tubular structure arranged between the second elastic part and the second rigid part, thereafter locking the first and second members to each other by a connection member. A pressure is exerted on the first and second ends of the tubular structure when those ends are arranged into the interconnected first and second members. The pressure is essential uniform around the circumference of the ends.

Further objects, features and advantages of the present invention will appear from the following detailed description, from the attached drawings as well as from the dependent claims.

BRIEF DESCRIPTION OF THE DRAWINGS

In order to explain the invention, a number of embodiments of the invention will be described below with reference to the drawings, in which:

FIG. 1A is a schematic exploded perspective view of a device according to a first embodiment of the invention, FIG. 1B is a schematic perspective view of a first rigid part of the device in FIG. 1A provided with catheters, FIG. 3A is a cross sectional view of the first rigid part of the device according to the first embodiment having a connection member integrally made with the rigid part, FIG. 3B is a perspective view of the first rigid part in FIG. 3A provided with catheters, FIG. 4A is a cross sectional view of a second rigid part of the device according to the first embodiment, FIG. 4B is a perspective view of the second rigid part in FIG. 4A, FIG. 5A is a perspective view of an axle and a top cone for the mounting tool according to the first embodiment before mounting side cone segments, and before arranging a rigid part thereto, FIG. 6A is a perspective view of the axle and top cone in FIG. 5A having the side cone segments mounted in position and the rigid part arranged thereto, FIG. 7A a perspective view of the mounting tool according to the first embodiment having a rigid part mounted thereto and ready for use, FIG. 8A shows a cross sectional view of a truncated cone comprising a receiving portion to receive a rigid part of the device before the arrangement of the rigid part, FIG. 5B is a perspective view of an axle and a top cone for the mounting tool according to the second embodiment, before arranging a rigid part provided with catheters thereto, FIG. 6B is a perspective view of the axle and the top cone in FIG. 5B with the catheters of the rigid part arranged thereto, before mounting side cone segments in position, FIG. 7B is a perspective view according to FIG. 6B after mounting the side cone segments in position and arranging the rigid part thereto, FIG. 8B is a perspective view of the mounting tool according to the second embodiment having a rigid part arranged thereto and provided with a guide before mounting an end tip to the guide, FIG. 12 is a schematic perspective view showing a first member of the device arranged at one end of the tubular structure, FIG. 13 is a schematic perspective view showing the first member arranged at one end of the tubular structure and a second member arranged at the other end of the tubular structure, FIG. 14 is a schematic perspective view according to FIG. 13 when the first and second members are interlocked, FIG. 15 is a schematic perspective view showing the device passing through the tubular structure when released after healing up the ends thereof, FIG. 16A is a side view of a device according to a second embodiment without the elastic parts mounted thereto, FIG. 16B is a cross sectional view along line A-A of the device in FIG. 16A, FIG. 17 is a cross sectional view of a portion of the device in FIG. 16A before interlocking the first and second rigid parts, FIG. 18 shows the device in FIG. 17 after interlocking the first and second rigid parts, FIG. 19 is a cross sectional view of a device according to an alternate embodiment, FIGS. 21-23 are schematic side views showing the mounting of the device to the tubular structure by means of a rectoscope.

Same reference numerals have been used to indicate the same parts in the figures to increase the readability of the description and for the sake of clarity.

DESCRIPTION OF EMBODIMENTS OF THE INVENTION

Figures 2A, 2B:
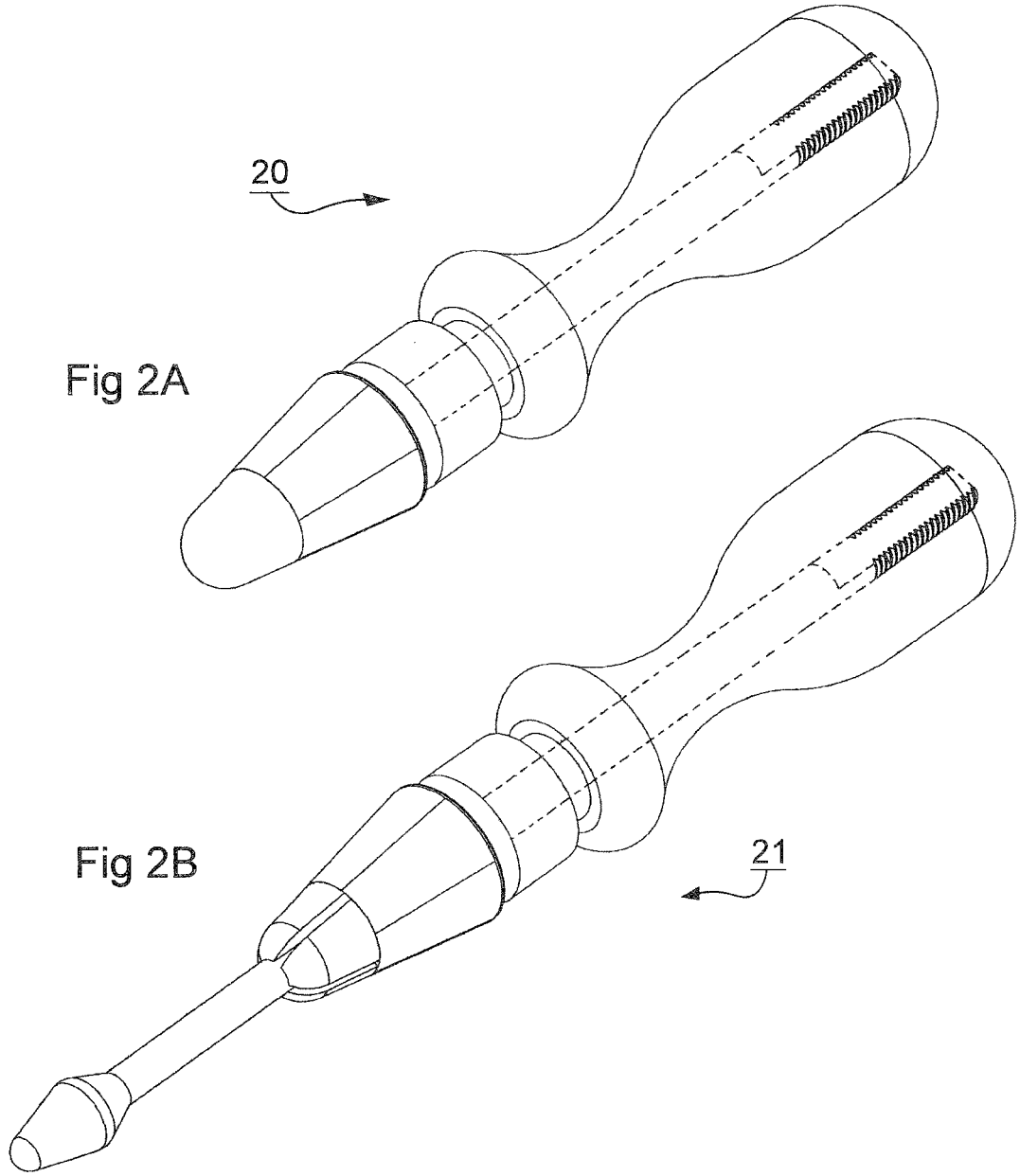
FIG. 2A is a schematic perspective view of a mounting tool according to a first embodiment for mounting a rigid part of the device in FIG. 1A to a tubular structure.
FIG. 2B is a schematic perspective view of a mounting tool according to a second embodiment for mounting the rigid part in FIG. 1B to a tubular structure.

Dehiscence of intestinal anastomosis is associated with high morbidity and mortality rates. Rapid and effective wound healing of intestinal anastomosis is critical for a safe and prompt recovery of patients, which are undergoing anastomotic surgery. Wound healing is a relatively stereotypical tissue reaction that follows a predictive sequence of events including acute inflammation, proliferation (cell division and matrix protein synthesis), and over time tissue remodeling for adaptation of the new tissue to the mechanical demands.

The unique property of the anastomotic device is that the wound healing process is initiated by local tissue ischemia and necrosis resulting in that previously intact tissue, i.e. the intestinal serosa of each of the divided segments of the tubular structure that are joined together by the anastomotic ring, fuse by a healing response initiated by the construction of the anastomotic device. It should be noted that in the abdominal cavity of a healthy living, the serosa of one segment of the intestine is in constant contact with the serosa of other segments of the intestine without being fused together, which otherwise would be potentially dangerous, e.g. if causing intestinal obstruction.

In contrast, the pressure maintained by the device creates a circumferential area of ischemia in the intestine, which provokes a tissue response leading to the healing process that seals together the two divided serosal sides of the intestine, and further leading to completion of the anastomosis.

On a molecular level, the ischemia provokes a local inflammatory reaction, including the recruitment of leukocytes and tissue oedema. Thus, local cells, such as macrophages and mast cells, which secrete cytokines and chemokines that provoke the extravasations of leukocytes into healing area, detect necrotic cells. Moreover, the local ischemia per se also stimulates macrophages and mast cells to secrete pro-inflammatory mediators.

Leukocyte recruitment is critical for the compression induced healing of intestinal anastomosis due to the compounds released by accumulated inflammatory cells, including radical oxygen species and metalloproteinase (MMP), which are necessary for the breakdown of the ischemic tissue as well as for breaking the integrity of the serosal surface.

MMPs are necessary for the breakdown of matrix proteins; especially important is collagen type 1, which is abundant in the intestinal submucosa, but also collagen of type III and V. The inflammatory cells predominately secrete MMP-2 and MMP-9, which both are active in the early phase of compression-induced healing of intestinal anastomoses.

The breakdown of the ischemic tissue is important for the tissue disintegration and release of the intestinal segment from the device. In addition, the serosal surface (visceral peritoneum) contains numerous mesothelial cells, which also respond to the ischemia by secreting potent MMPs and angiogenetic factors.

The broken integrity of the serosal surface is a precondition for the unique healing process induced by the device knowing that the serosal side of the intestines normally exerts anti-adhesive functions avoiding adhesions between intestinal segments in the abdominal cavity. In parallel, intestinal fibroblasts and epithelial cells respond to the ischemic necrosis induced by the CARP-device by secreting angiogenetic factors, including vascular endothelial growth factor, which stimulates the growth of new blood vessels in the healing tissue.

Moreover, in this complex reaction, intestinal fibroblasts and epithelial cells also secrete metalloproteinases (MMP-1, MMP-7 and MMP-10), which contribute to the breakdown of matrix proteins and resolution of the tissue paving the way for the compression induced healing of anastomoses.

FIG. 1A is an exploded view of a device 10 according to a first embodiment. The device 10 comprises a first member comprising a first rigid part 11 and a second elastic part 12, a second member comprising a second rigid part 13 and a second elastic part 12, a sealing 14 and a connection member 15. The rigid parts 11, 13 and the elastic parts 12 have a generally hollow open configuration.

According to the first embodiment of the device 10, the connection member 15 is integral with the first rigid part 11. The first member and the second member are interlockable to each other, as a male-female component, by the connection member 15.

FIG. 1B shows the first rigid part 11 provided with four catheters 16 mounted to four holes 17 (see FIG. 3B) symmetrically arranged around the annular wall of the first rigid part 11 opening at the outer side thereof, forming a free passage through each catheter, which further elongates through the hole.

The rigid parts 11, 13 and the elastic parts 12 are made of a polymeric material, more specifically a biocompatible material and most specifically a biodegradable material.

The elastic parts 12 have a cross section, which may be of any shape, for example circular, elliptic, rectangular or flat, and which has a diameter of about 2 to 9 mm, or more specifically 4 to 8 mm, or most specifically 5 to 7 mm. The elastic parts 12 are substantial circular symmetric rings and are made as a compact body or as a tube, which may be filled with air, gas or fluid, and are made of an elastic polymeric material of for example 40 to 70 Shore. The elastic parts 12 have an inner diameter that is smaller than the smallest outer diameter of the rigid parts 11, 13 as will be explained below.

FIG. 2A shows a mounting tool 20 according a first embodiment, and FIG. 2B shows a mounting tool 21 according to a second embodiment. The mounting tools 20, 21 are required for arranging the device 10 to a tubular structure, which will be described in detail below.

As shown in FIG. 3A, the first rigid part 11 according to the first embodiment has a substantially cylindrical inner surface, which is flared out at a non-connecting end 30. The outer surface is profiled and forms a partly semi-circular surface between the non-connecting end 30 and the connecting end. The diameter at the non-connecting end 30 is larger than or equal to the diameter at the connecting end. A radial surface 34 is provided at the connecting end delimiting the partly circular contour. The edge 35 of the non-connecting end 30 is slightly bevelled, and the surface 34 ends in an edge 36 connecting the surface 34 with the semi-circular surface.

The connection member 15 is integral with the first rigid part 11, as shown in FIG. 3A, and is provided with transversal slits 37 from the free end thereof around the periphery forming tongues 38 between the slits 37. At least one of the tongues 38 is provided with an outward protrusion 39 arranged adjacent or at a distance from the free ends of the tongues. The number of slits 37 may vary and the length of the slits 37 can be as long as the entire width of the connection member 15, as illustrated in FIG. 3A, or be shorter. The slits 37 are either symmetrical or unsymmetrical provided around the periphery, forming tongues with a similar or varying width. FIG. 3B shows as an example, the connection member 15 having six tongues without protrusions and six tongues with protrusions, which are arranged symmetrical around the periphery, wherein the tongues with protrusions have a width smaller than the tongues without protrusions. The number of tongues can vary, for example 2-10 may be provide, which can be arranged symmetrical or unsymmetrical around the periphery. The connection member 15 has a circumferential recess 31 around its outer diameter to accommodate the sealing 14.

The second rigid part 13 has a substantially cylindrical inner surface that is flared out at a non-connecting end 40, as seen in FIG. 4A. The outer surface is profiled and forms a partly semi-circular surface between the non-connecting end 40 and a connecting end 41, the outermost edge 47 at the non-connecting end 40 being slightly bevelled. The diameter at the non-connecting end 40 is larger than or equal to the diameter at the connecting end 41. A bevel 42 is provided at the connecting end 41 to facilitate insertion of the connection member 15 into the second rigid part 13, as will be explained below. A surface 44 is provided at the connecting end 41 due to the partly circular contour. The surfaces 34 and 44 are equal in size and ends in the edge 36 and an edge 46, respectively. Grooves 45, or threads, are provided on the cylindrical inner surface of the second rigid part 13 and are arranged at the portion adjacent the connecting end 41. A locking function is obtained at engagement between the protrusions 39 and the grooves 45 for interlocking the first member and the second member by the connection member 15.

With reference to FIG. 5A, the mounting tool 20 according to the first embodiment comprises a rigid rod 50 forming a central axle having a top cone 51 at one end and provided with threads 52 at the other end. The top cone has a closed distal end and is integral with the axle. The tool 20 further comprises a truncated cone which is formed by several side cone segments 54, for example 6-8 segments. The truncated cone has a small diameter end abutting the top cone and a broad diameter end having a profiled section 55. Furthermore, the mounting tool 20 comprises a cylinder 56 and a handle 57 with an end-hat 58. The elements of the tool 20 are coaxially held together by the rod due to their symmetrically arranged bores. The mounting tool 20 comprises a receiving portion 48 for receiving the rigid parts 11, 13 comprising the profiled section of the large end of the truncated cone, which is dimensioned to receive the non-connecting end 30, 40 having a bevelled edge 48', as shown in FIG. 8A for the rigid part 13. The tool 20 also comprises a conical portion comprising the top cone and the truncated cone including the cone segments. The conical portion has a releasable portion comprising the cone segments. FIG. 5A shows a rigid part 11, 13 that is to be arranged at the receiving portion, and cone segments, which are to be arranged on the central axle between the top cone and the rigid part for forming a circular cone having a smooth transition to the rigid part, as shown in FIG. 6A. The broad diameter end of the truncated cone is equal or slightly wider than the outer diameter of the rigid part. The cylinder has a recess (not shown) on the side facing the rigid part to accommodate the connection member 15 when this is integral with the first rigid part 11. The side cone segments between the top cone and the rigid part abutting the cylinder are firmly fastened in position, since all the elements mentioned are held together by the handle, which is non-rotational fixed by the end-hat. When the mounting tool 20 is used to arrange the second rigid part 13, the cylinder is turned 180° around the rod so that the circular recess is facing the handle.

In an alternate embodiment, the cylinder may be integral with the handle. In another alternate embodiment, a cylindrical section may be provided for the arrangement of the side cone segments around the rod.

The mounting tool 21 according to a second embodiment is used for mounting a device 10 having a first rigid part 11 of the first embodiment provided with catheters 16. The mounting tool 21 of the second embodiment differs from the first one 20 in that the central axle 50 is provided with recesses 59 symmetrically arranged along the axle at the distal end, and the recesses are elongating through the top cone to each accommodate one catheter, as shown in FIGS. 5B and 6B. The recesses are opening into a hole 60 at the upper part of the top cone 51', where the catheters 16 will exit, see FIG. 7B. A flexible annular guide 61 with an end-tip 62 is provided and arranged at the hole to accommodate and stabilize the catheters, as shown in FIG. 8. The rest of the description of the mounting tool 21 according to the second embodiment is similar to the description above of the mounting tool 20 according to the first embodiment.

The rod is for example made of a metallic or polymeric material. The top cone and the cone segments are for example made of a polymeric material, stainless steel or another metallic material. The rest of the elements of the tool 20, 21 are made of a polymeric material, stainless steel or another metallic material.

Figure 9:
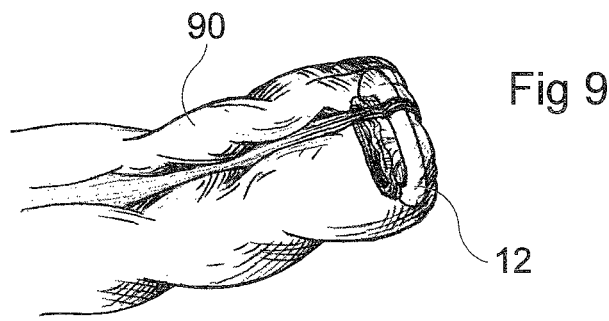
FIG. 9 is a schematic perspective view of an elastic part arranged inside a tubular structure at one end thereof, the edge of this end being folded over the elastic part.
Figure 10:
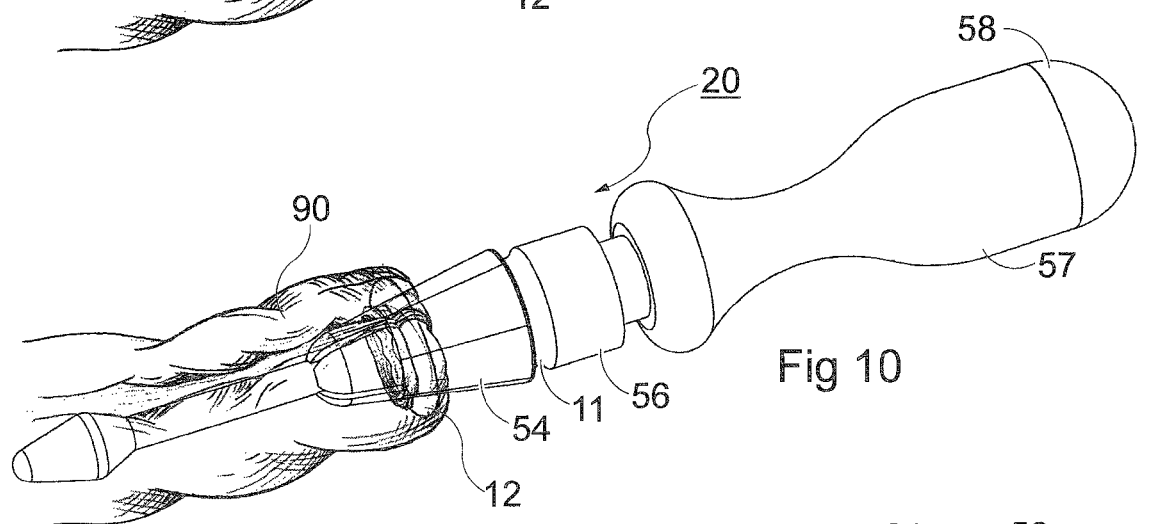
FIG. 10 is a schematic perspective view according to FIG. 9 showing the mounting tool according to the second embodiment inserted into the tubular structure before mounting the elastic part on the first rigid part.
Figure 11:
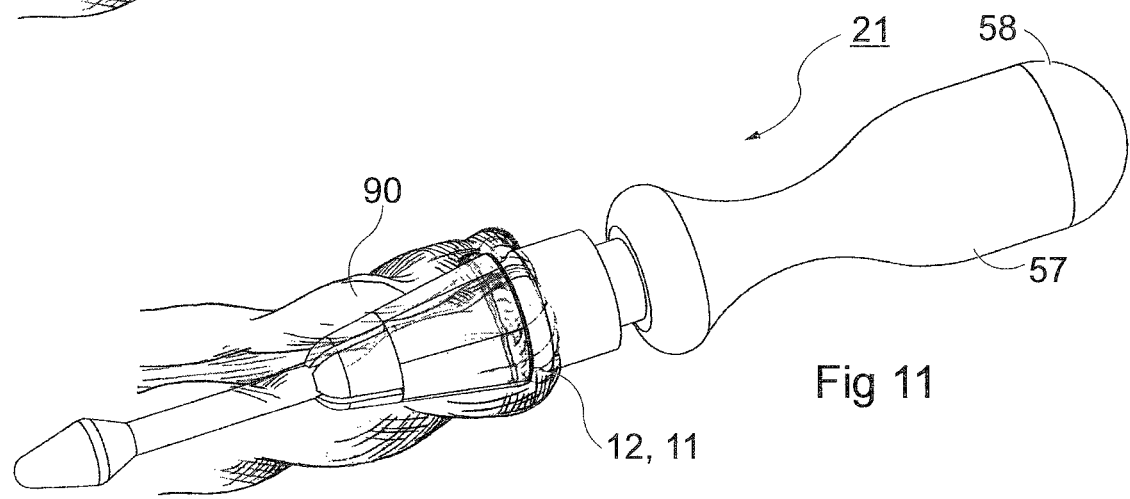
FIG. 11 is a schematic perspective view according to FIG. 10 showing the elastic part mounted on the first rigid part.

Reference is made to FIG. 9-11 for describing the mounting of the device 10 to a tubular structure 90 having a first end 120 and a second end 121, which are to be fused together. In the example described, the device 10 has a first rigid part 11 provided with catheters 16, hence the tool 21 according the second embodiment is used for performing the mounting. The rigid part 11 is initially arranged at the receiving portion of the tool 21 having the connection member 15 arranged into the circular recess of the cylinder 56 as described above. The elastic part 12 is arranged inside the tubular structure 90 at one end 120, and the edge of this end 120 is folded over the elastic part 12, as shown in FIG. 9. The tool 21, with the rigid part 11 arranged into the profile 48 of the truncated cone and with the catheters arranged into the recesses 59 along the axle 50 and elongating through the guide 61, is inserted into the tubular structure 90 from the folded end 120, as shown in FIG. 10, expanding the elastic part 12, which is surrounded or wrapped on three sides by the tubular structure 90, until it is snapped around the circumference of the rigid part 11. The elastic part 12 is then locked to the rigid part 11 due to its partly semi-circular contour forming a recess, as illustrated in FIG. 11. This snapping-operation requires of an operator to keep firm hold of the end 120 with the elastic part 12 arranged thereto by one hand and of the tool 21 by the other hand. For releasing the first member 11 from the tool 21, firstly, the end-hat 58 is released. In order to prevent that the tool 21 and the rigid part 11 are rotating and damaging the tubular structure, it is necessary to keep a firm grip of the handle 57, which is locked for rotation in relation to the axle 50 due to plane surface on the axle at the threading, then the handle is removed from the axle. Thereafter the cylinder 56 is released and removed. Now when the axle 50 is free the truncated cone comprising the side one segments 54 is falling apart and are removed by a pair of forceps through the opening formed due to the rigid part 11. Then, the first member is pushed off the axle 50 over the top cone.

The operation described is repeated for arranging the second rigid part 13 to the other end 121 of the tubular structure 90 by using either the mounting tool of the first 20 or second 21 embodiments. Thus, the first and second members of the device 10 is formed with the end 120, 121, respectively, having the tubular structure 90 arranged between the rigid part 11, 13 and the elastic part 12. Thus, a single layer of the tubular structure 90 is squeezed between a rigid part 11, 13 and an elastic part 12.

The extremity of the first end 120, when folded and arranged between the first rigid part 11 and the elastic part 12, forms a first lip or a contact surface 130 that is essentially circular, as seen in FIG. 13. Similarly, the second end 121 forms a second lip or contact surface 131. An essentially uniform and equal pressure is exerted on the contact surfaces 130, 131 all over the periphery.

The final action for forming the device 10 is to connect the first member and the second member by the connection member 15, which is performed by a simple press action by hand by the operator. In the first embodiment the connection member 15 is integral with the first rigid part 11, and the first member including the connection member 15 and the second member are joined together by interlocking the members by hand. The tongues 38, of which some or all, have protrusions 39 arranged on the connection member 15 interact with the grooves 45 arranged on the inner surface of the second rigid part 13 and perform a locking action. Thus, the connection member 15 engages the second rigid part 13, and the first and second members are fixedly mounted to each other.

The first and second members are dimensioned so that a gap appears between the surfaces 34 and 44 (see FIGS. 3 and 4) when the members are interlocked without arrangement of the two ends 120, 121 of the tubular structure 90 between the rigid parts 11, 13 and the elastic parts 12, respectively. When interlocking the first member and the second member with the tubular structure 90 arranged thereto, the gap still exists between the surfaces 34 and 44, and the contact surfaces 130, 131 are pressed against each other. The ends 120, 121 are compressed between the elastic parts 12, 14 and the rigid parts 11, 12, respectively, resulting in that the ends 120, 121 will slightly creep into the gap and hang over the edges 44 and 36, respectively.

A contact area 201 is created between the contact surfaces 130 and 131, and a point of necrosis 202, or rather a line of necrosis, is defined as the point where the tubular structure 90 is pressed against the edges 44 and 36 by the pressure from the elastic parts 12, respectively, as shown in FIG. 21. The contact area 201 and the point of necrosis 202 have a major importance in the necrosis process.

In an alternative embodiment illustrated in FIG. 19, the connection member, which is integral with the first rigid part 191, has one or several circumferential grooves 192 around the periphery. In this case, the second rigid part 193 has a protrusion 194 arranged around the inner periphery adjacent the connecting end for engagement with the notch(es) 192 to interlock the first rigid part 191 and the second rigid part 192.

A second embodiment of an anastomotic device 200 will now be described with reference to FIGS. 16A, 16B, 17, and 18. The device 200 comprises a first member, a second member and a connection member 160, each of a hollow open configuration. The first and second members are identical, each comprising a rigid part 13 and an elastic part 12, wherein the rigid parts 13 have the same configuration as the second rigid part 13 according to the first embodiment of the device 10. The connection member 160 is made as a substantially cylindrical separate piece, i.e. separated from the first and second member, and has notches 170 (see FIG. 17) arranged on the outer surface thereof for engagement with the grooves 45, or threads, provided on the internal cylindrical surface of the rigid parts 13. The connection member 160 is dimensioned for interlocking the first and second member when arranged inside the rigid parts 13, as illustrated in FIG. 18. Recesses 172 may be provided, for example symmetrically, on the outer surface of the connection member 160, each to accommodate a circular sealing member (not shown), such as an O-ring. The connection member 160 has optionally at least two holes 161 passing through the annular wall of the connection member 160, for example at the centre symmetry line. At least two nipples (not shown) can engage this/these hole(s) 161 for the connection of at least two tubes or catheters, which will be explained below. FIG. 17 shows the first and second rigid part 13 and the connection member 160 before interlocking. FIG. 18 shows the identical first and second rigid parts 13 interlocked by the connection member 160. A distance or a gap 180 is provided between the surfaces 87 of the rigid parts 13.

The pressure that is exerted on the contact surfaces 130, 131 at the ends 120, 121 of the tubular structure 90, when arranged in the device 10, 200, can be increased or decreased by adjusting the size of the gap 203, 180. In the case with the device of the first embodiment 10, the gap 203 may be varied by arranging the notches 39 on the connection member 15 closer or less closer to the free ends of the tongues 38. When using the device according to the second embodiment 200, the gap 180 may be varied by arranging the connection member 160 deeper or less deep inside the rigid parts 13 in relation to a reference position.

The hollow open configuration of the first and second members and the connection member 160 are shown as being essentially circular from a side view, see FIG. 18, but can be of any other shape, e.g. elliptic or oval, or partly rectangular or triangular, and can be segmented, as shown in FIG. 16B.

Figure 20B:
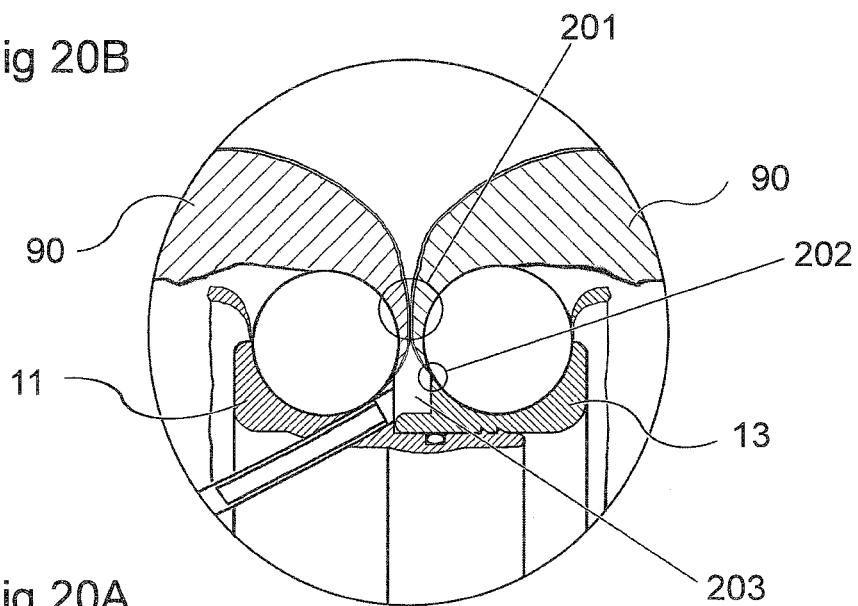
FIG. 20B is an enlarged view of the encircled area in FIG. 20A showing the contact area and the point of necrosis.
Figure 20A:
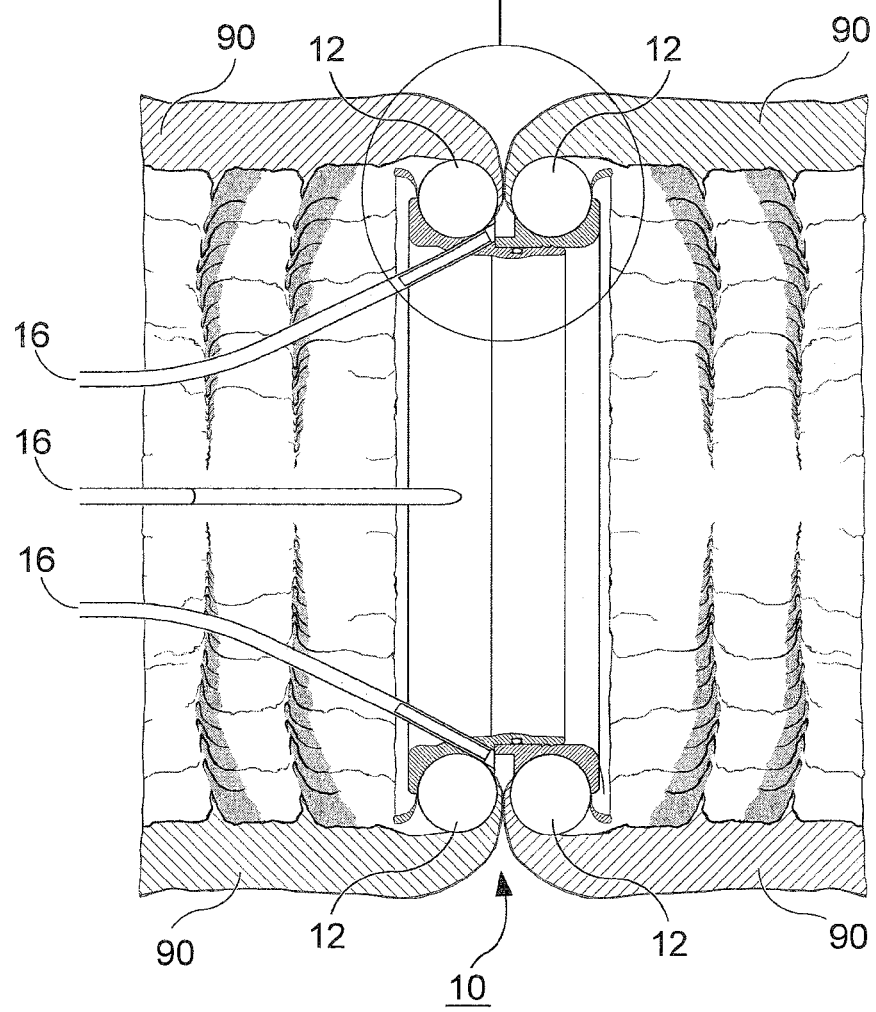
FIG. 20A is a schematic cross sectional view showing the device according to the first embodiment provided with catheters and arranged to the tubular structure fusing the ends thereof.

FIG. 20A illustrates the device 10 of the first embodiment arranged to a tubular structure 90. The catheters 16 are arranged to the holes 17 and are elongating through the tubular structure 90. The first ends of the catheters 16 that are arranged to the holes are opening into the cavity 203, and the second ends of the catheters 16 are exiting through rectum. The guide 61 is removed when the second ends of the catheters have exit. These ends of the catheters can be connected to for example syringes, pumps or other devices used for supervising or controlling the healing up of the ends of the tubular structure. It is also possible to supply different fluids to the cavity 203, such as grow stimulating substances or contrast media, as will be explained below.

The enlarged view 20B shows the compression of the tubular structure 90 between the elastic parts 12 and the rigid parts 13.

The tubular structure 90 will swell up at the ends 120, 121, thus closing the gap between the surfaces 34 and 44, forming a closed cavity 203 defined by the compressed tubular structure 90, the connection member 15 and the surfaces 34 and 44 of the rigid parts 11, 13. A contact area 201 is created between the contact surfaces 130, 131, and a point or line of necrosis 202, which is defined as the point 202 where the tubular structure 90 is pressed against the edges 36 and 46 by the pressure from the elastic part 12. The blood stream or circulation at the ends 120, 121 of the tubular structure 90 is cut off (strangled) and ceases right up to the point of necrosis 202. Tissue regeneration takes place at the contact area 201, which will result in fusing together the two ends 120, 121 of the tubular structure 90. When the two ends of the tubular structure are fused, i.e. have healed up, the device 10, 200 is automatically released and leaves the tubular structure following the faecal stream through rectum.

FIG. 20A shows the catheters 16 fastened to the device 10 and arranged inside and along the tubular structure 90. By means of the guide 61, the ends of the catheters are passing out of the tubular structure 90 through rectum.

It is possible to supply different fluids to the cavity 203 by means of the catheters 16. For example, a certain selected liquid may be supplied to the cavity 203, in a continuous or an intermittent flow. The liquid can be tissue grow stimulating, or perform any other actions for accelerating the healing, such as stimulating the recruitment of leukocytes and/or secretion of cytokines and chemokines.

Furthermore, contrast medium may be supplied through the catheters 16 for performing a radiological control of the anastomos, for example regarding closeness or contrary leakage, which is especially important directly after mounting the device to the tubular structure. By supplying a certain pressure of the supplied liquid to one catheter, while keeping the other catheters closed, a measure of the pressure for leakage is obtained. In this manner, a possibility is provided to continuously supervise the healing process of the two ends of the tubular structure. In case of a minor leakage of the anastomos, it is possible to apply a sub-pressure or slight vacuum to the cavity 203 by simply connecting one catheter to a vacuum air pump (not shown).

The discussion above regarding supply of selected fluids may also be applied when using the device 200,190. Different fluids may be supplied to the cavity 203 by means of thin catheters or tubes that are connected to the connection member 160 by nipples arranged to the holes 161. Furthermore, contrast medium may be supplied for performing a radiological control of the anastomos, for example regarding closeness or contrary leakage, which offers a possibility to continuously supervise the healing process. In case of a minor leakage of the anastomos, it is possible to apply a sub-pressure or slight vacuum to the cavity 203 by simply connecting one end of a catheter to the hole 161 by a nipple and the other end to a vacuum air pump (not shown).

FIGS. 21, 22, 23, show the arrangement of a device 10 close to rectum (a low anastomos, wherein the first rigid part 11 is provided with catheters 16. FIG. 21 shows a recto scope 210 that is inserted into the tubular structure 90, which has a sealed end 211. The recto scope 210 comprises an inner sleeve and an outer sleeve 212. The front edge of the inner sleeve has a recess wherein the elastic part 12 of the device 10 is fastened. The recess is adapted to the inner diameter of the elastic parts 12. The recto scope 210 is connected to a vacuum suction pump by a pipe or tube 213 and a controller (not shown), e.g. a computer.

The recto scope comprises a handle 214 including a removable lens 215 and a hole 216. Airflow to the vacuum suction pump normally passes through the hole of the handle and has no influence on the tubular structure 90. By covering the hole on the handle with a fingertip, e.g. forefinger, a vacuum is developed inside the recto scope resulting in that the sealed end of the tubular structure is sucked into the recto scope. The catheters arranged to the first rigid part 11 are arranged inside a grooved flexible tube 217 having a releasable sharp tip 218 at one end and a funnel 219 at the other end. The tube is inserted into the sealed end 211, and exits through the hole when the lens 215 is removed, as shown in FIG. 22. The rigid part 13 is then arranged close to the elastic part 12, and by means of the second sleeve 212 of the recto scope 210 the elastic part 12 is mounted around the circumference of the rigid part 11. The described mounting process can be compared with the process described according to FIGS. 9-11, and hence the process can be continued in accordance to FIG. 12-15. FIG. 23 shows the first end 120 and the second end 121 of the tubular structure 90 having the first and second member mounted thereto before interlocking those members. Finally, the closed end 211 is cut open by inserting a suitable tool into the recto scope 210.

Herein above, several embodiments of the invention are described with reference to the drawings in order to enable a skilled person to perform the invention. However, the features and method steps included in these embodiments do not limit the invention. Moreover, the features and method steps may be combined in other manners than specifically described.

The cross sections of the elastic parts 12 are shown as substantially circular. However, other shapes may be used, such as rectangular, triangular, hexagonal, octagonal, etc. The outer surface of the rigid parts 11, 13 comprises a recess intended to receive the elastic parts 12 respectively. This recess has a shape that is at least partly complementary to the shape of the elastic part 12. Thus, the recess may be rectangular, triangular, hexagonal, octagonal, etc.

The configuration or outer shapes of the elastic parts 12 are shown to be substantially cylindrical having a circular outer contour. However, other shapes are possible, such as rectangular, triangular, hexagonal, octagonal etc.

The elastic parts can be only partially elastic. The elasticity is used for squeezing the tubular structure 90 between the elastic parts 12 and the rigid parts 11, 13, respectively, with a certain force. Other means performing the same function is possible to use.

In an alternate embodiment, the top cone may be snapped onto the central axle, as well as the end-hat of the handle. Furthermore, the truncated cone can be made as a whole piece, which can be released from the axle through rectum at low anastomoses.

In the claims, the term "comprises/comprising" does not exclude the presence of other elements or steps. Furthermore, although individually listed, a plurality of means, elements or method steps may be implemented. Additionally, although individual features may be included in different embodiments, these may possibly be combined in other ways, and the inclusion in different embodiments does not imply that a combination of features is not feasible. In addition, singular references do not exclude a plurality. The terms "a", "an" does not preclude a plurality. Reference signs in the claims are provided merely as a clarifying example and shall not be construed as limiting the scope of the claims in any way.

The invention claimed is:

1. A method for connecting opposing ends of a severed tubular structure, such that anastomosis will occur between the severed ends, utilizing a anastomotic device comprising a generally hollow open first connector assembly that includes a first elastic ring elastically disposable on a first rigid part, a separate generally hollow open second connector assembly that includes a second elastic ring elastically disposable on a second rigid part, and a connection member structured and operable to interlockingly connect the first and second rigid parts, said method comprising:
    (a) arranging the first elastic ring inside an introverted fold of a first end of a severed tubular structure;
    (b) mounting the first elastic ring on the first rigid part such that a portion of the introverted fold of the first end of the tubular structure is bound between the first elastic ring and the first rigid part;
    (c) arranging the second elastic ring inside in introverted fold of an opposing second end of the severed tubular structure;
    (d) mounting the second elastic ring on the second rigid part such that a portion of the introverted fold of the second end of the tubular structure is bound between the second elastic ring and the second rigid part; and
    (e) interlockingly connecting the first and second rigid parts to each other utilizing the connection member, thereby placing the first and second ends of the severed tubular structure in contact with each other such that anastomosis will occur between the first and second ends of the severed tubular structure.

2. The method according to claim 1, wherein interlockingly connecting the first and second rigid parts comprises connecting the first and second members such that pressure is exerted between the contacting first and second ends of the severed tubular structure such that a contact surface is established between the severed first and second ends around the entire circumferences of the severed first and second ends.

3. The method according to claim 2, wherein the pressure is essentially uniform around the circumference of the contact surface between the first second ends of the severed tubular structure.

* * * * *